(12) United States Patent
Campan

(10) Patent No.: US 10,690,645 B2
(45) Date of Patent: Jun. 23, 2020

(54) SMART MEASUREMENT SYSTEM AT THE DELIVERY POINT OF A FLUID

(71) Applicant: SUEZ GROUPE, Paris la Defense (FR)

(72) Inventor: Francis Campan, Antony (FR)

(73) Assignee: SUEZ GROUPE, Paris la Defense (FR)

( * ) Notice: Subject to any disclaimer, the term of this patent is extended or adjusted under 35 U.S.C. 154(b) by 0 days.

(21) Appl. No.: 15/329,610

(22) PCT Filed: Jul. 28, 2015

(86) PCT No.: PCT/IB2015/055689
§ 371 (c)(1),
(2) Date: Jan. 27, 2017

(87) PCT Pub. No.: WO2016/016803
PCT Pub. Date: Feb. 4, 2016

(65) Prior Publication Data
US 2017/0219550 A1    Aug. 3, 2017

(30) Foreign Application Priority Data

Jul. 30, 2014 (FR) .................................... 14 57363

(51) Int. Cl.
*G01N 33/18* (2006.01)
(52) U.S. Cl.
CPC ......... *G01N 33/18* (2013.01); *G01N 33/1886* (2013.01); *G01N 33/1893* (2013.01)
(58) Field of Classification Search
CPC . G01N 33/18; G01N 33/1893; G01N 33/1886
See application file for complete search history.

(56) References Cited

U.S. PATENT DOCUMENTS

| 8,479,598 B2 | 7/2013 | Vincent |
| 2008/0052012 A1 | 2/2008 | Howell et al. |

(Continued)

FOREIGN PATENT DOCUMENTS

| CN | 102803653 A | 11/2012 |
| CN | 103026226 A | 4/2013 |
| FR | 2 929 752 A1 | 10/2009 |

OTHER PUBLICATIONS

International Search Report, dated Oct. 5, 2015, from corresponding PCT Application.

(Continued)

*Primary Examiner* — Paul M. West
(74) *Attorney, Agent, or Firm* — Young & Thompson

(57) ABSTRACT

Disclosed is a device for measuring at least one physical, chemical or biological parameter of a fluid, flowing in a pipe belonging to a fluid-distribution network, the device being installed in a cut on the pipe at the fluid delivery point, the pipe thus including a first section and a second section, the device including at least one sensor provided with a measurement end. The device also includes: a body including an opening forming a flow line, and at least one insertion recess capable of receiving the measurement end of the at least one sensor, the insertion recess opening into the flow line; an attachment unit arranged to connect a first end of the flow line with an end of the first section and a second end of the flow line with an end of the second section, to allow the fluid to flow through the flow line.

20 Claims, 1 Drawing Sheet

(56) References Cited

U.S. PATENT DOCUMENTS

| | | | |
|---|---|---|---|
| 2010/0085211 A1 | 4/2010 | Wang et al. | |
| 2010/0313674 A1* | 12/2010 | Dutel | G01F 1/7086 |
| | | | 73/861 |
| 2011/0037615 A1 | 2/2011 | Borlee | |
| 2013/0205879 A1 | 8/2013 | Genin et al. | |
| 2014/0216167 A1* | 8/2014 | Nielsen | G01F 1/667 |
| | | | 73/861.28 |
| 2015/0300851 A1* | 10/2015 | Isik-Uppenkamp | G01F 1/584 |
| | | | 73/861.12 |

OTHER PUBLICATIONS

Office Action issued in Chinese Patent Application No. 201580040692.5 dated Feb. 3, 2020 with English translation provided.

* cited by examiner

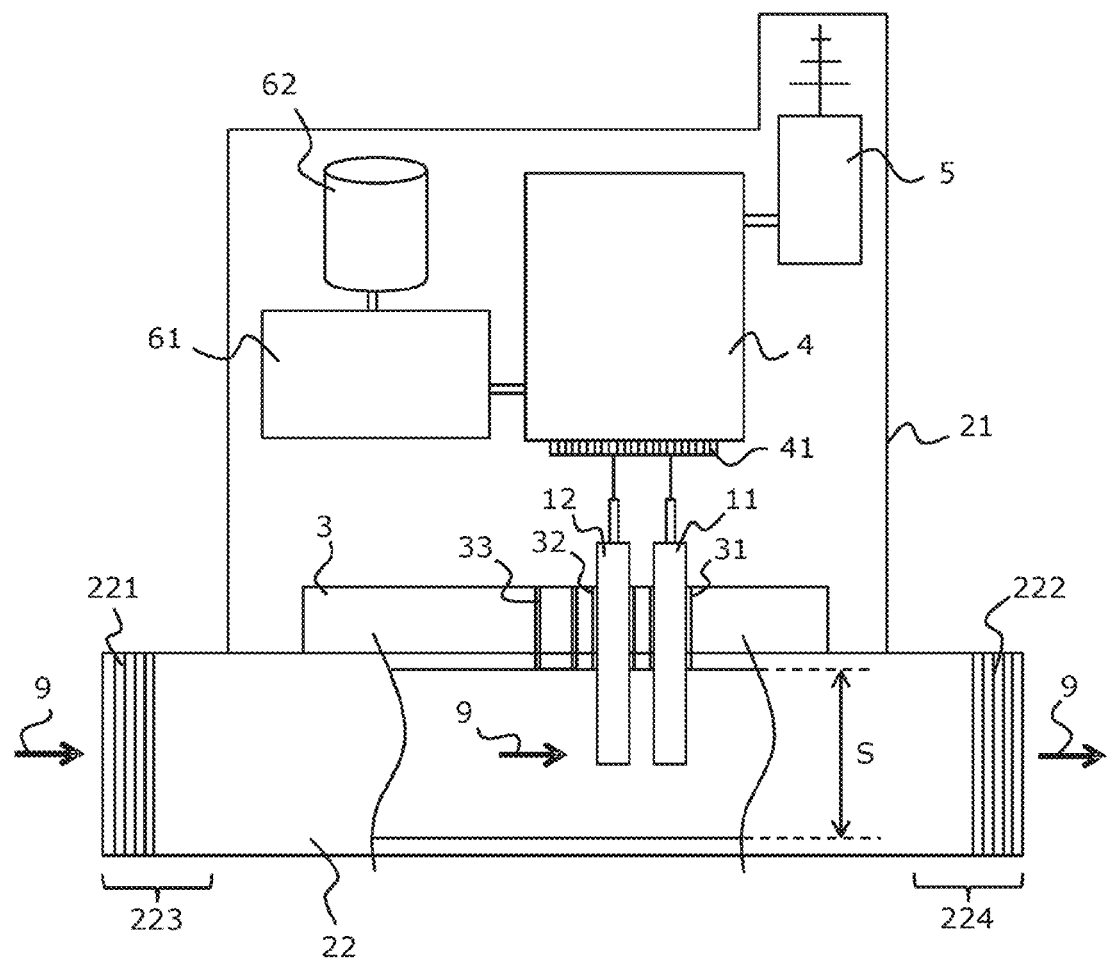

SMART MEASUREMENT SYSTEM AT THE DELIVERY POINT OF A FLUID

TECHNICAL FIELD

The present invention relates to the field of the online measurement devices measuring at least one physical, chemical or biological parameter of a fluid, in particular of water or of gas, flowing in a pipe of a fluid supply system, in particular in a distribution network.

The present invention relates more particularly, but not exclusively, to such devices installed at the point of delivery of the fluid, the point of delivery denoting the point of the network where the fluid is delivered to a user.

PRIOR ART

Different equipment items are known from the prior art that are intended to measure one or more parameters of a fluid flowing in a distribution network, particularly in the field of potable water distribution.

A first type of known equipment is a probe provided with a set of sensors capable of detecting parameters such as chlorine, conductivity, pressure or even temperature of the fluid.

The U.S. Pat. No. 8,479,598 B2 describes a probe comprising a body provided with a measurement head, particularly of cylindrical form, and several sensors mounted at one of the ends of this measurement head. The measurement head comprises housings arranged so as to be able to insert sensors therein axially or radially.

Such a multi-sensor probe is typically mounted in a pipe by insertion of the measurement head in a radial direction relative to the pipe.

The insertion of a multi-sensor probe into a pipe entails producing an opening on the periphery of the pipe, for example a threaded cylindrical hole that makes it possible to receive a screwthread formed on the body of the probe.

A multi-sensor probe typically comprises means for collecting data from measurements performed by the sensors and means for communicating these data.

For example, the Intellisonde™ product from the company "Intellitect Water" makes it possible to measure and record values measured by one or more sensors at regular intervals, for example every hour or every minute. The measured values are for example transmitted by a computer standard of wireless network type (for example GPRS) or by Ethernet protocol. In terms of autonomy, this product is equipped with embedded electric batteries ensuring operation typically for a period of six months.

The multi-sensor probe has several drawbacks. Its full ownership cost is high because, in addition to the purchase cost, the correct operation thereof notably requires recalibration or part replacement operations. Furthermore, its energy autonomy is limited in light of the desired measurement data recording and communication frequencies and its dimensions do not make it possible for it to be installed on most pipes at the point of delivery.

These drawbacks make the multi-sensor probe inappropriate to the deployment of this type of equipment at fluid delivery points.

A second type of known equipment relates to a system for remotely reading fluid meters, notably water meters, as described in the patent FR 2 929 752 B1. This document describes a system for reading and transmitting values measured by at least one measurement sensor. This system comprises a transmitter for the transmission of measurement values and a receiver, typically installed remotely, capable of collecting the values transmitted by the transmitter.

Such a remote reading system is typically powered by an electric battery.

The power supply means (battery) of a remote reading system allows for a relatively low measurement data recording and communication frequency, typically of the order of one transmission per day, to achieve a satisfactory energy autonomy, for example of the order of several years. Such a power supply means is however insufficient for performing a collection of additional measurements, for example using a multi-parameter probe.

Furthermore, the equipment items that have just been described are generally equipped with very simple signal processing programs, making the parameterizing of the measurement and measurement data processing operations suboptimal, and consequently increasing the overall operating costs.

One aim of the present invention is to propose a device for measuring at least one parameter of a fluid which is energy autonomous, notably in order to be able to install it at any point of the existing distribution networks, including when no external energy source is available.

Another aim of the present invention is to propose a device for measuring at least one parameter of a fluid that can be installed at a point of delivery of the fluid.

Yet another aim of the present invention is to propose a device for measuring at least one parameter of a fluid capable of measuring different physical, biological or chemical parameters of the fluid.

Another aim of the present invention is to propose a device for measuring at least one parameter of a fluid capable of transmitting information to a remote computer terminal, notably in order to signal distribution anomalies or even modifications of fluid properties.

Another aim of the present invention is to propose a device for measuring at least one parameter of a fluid provided with embedded intelligence, notably in order to detect anomalies in the distribution or else modifications of properties of the fluid, and transmit an alert linked to any anomaly as soon as the latter occurs.

Yet another aim of the present invention is to propose a device for measuring at least one parameter of a fluid that can be remotely parameterized.

Another aim of the present invention is to propose a device for measuring at least one parameter of a fluid having an optimized energy autonomy, particularly to make it possible to perform measurements and transmit measurement data at high frequencies.

Another aim of this invention is to propose a device for measuring at least one parameter of a fluid capable of transmitting measurement data in real time.

More generally, one aim of the present invention is to propose a device for measuring at least one parameter of a fluid that simplifies the installation and maintenance operations and reduces the operating constraints.

SUMMARY OF THE INVENTION

This objective is achieved with a device for measuring at least one physical, chemical or biological parameter of a fluid, in particular of water or gas, flowing in a pipe belonging to a fluid distribution network, this device being intended to be installed as cutoff on said pipe at the point of delivery of the fluid, said pipe thus comprising a first section and a second section, this device comprising at least one sensor provided with a measurement end, characterized in that it further comprises:
- a body comprising an opening forming a flow pipe, and at least one insertion housing capable of receiving said measurement end of the at least one sensor, the insertion housing emerging in the flow pipe,
- fixing means arranged to connect:
  - a first end of the flow pipe to an end of the first section of the pipe,
  - a second end of the flow pipe to an end of the second section of the pipe, so as to allow the fluid to flow through the flow pipe.

Advantageously, the average internal section of the flow pipe is substantially identical to the average internal section of the pipe.

One advantage of such a device is that it can be manufactured in a number of limited series in which the average internal section corresponds to the typical average internal sections of the pipes of the existing fluid distribution networks, for example with a diameter of 20 mm.

The "in line" configuration, that is to say by connection of the flow pipe in the extension of the pipe, greatly simplifies its installation (see later, the installation method associated with this device).

According to a very advantageous particular feature of the invention, the device further comprises a smart module capable of:
- triggering at least one measurement by the at least one sensor at determined time intervals,
- diagnosing an anomaly of at least one physical, chemical or biological parameter of the fluid as a function of at least one measured value.

According to another advantageous particular feature of the invention, the smart module further comprises communication means capable of carrying out a computerized communication between the smart module and a remote computer terminal, the smart module being arranged to transmit to the computer terminal information relating to the diagnosed anomaly.

According to yet another advantageous particular feature of the invention, the instant of the transmission of the information relating to the diagnosed anomaly is determined by the instant at which said anomaly is diagnosed. In other words, this information is transmitted as soon as an anomaly is diagnosed, or after a very short time period.

Or, the smart module is arranged to transmit to the computer terminal information relating to the diagnosed anomaly at regular time intervals if an anomaly is diagnosed, that is to say that the information is transmitted if and only if an anomaly is diagnosed.

The presence of an embedded smart module capable of locally processing measurement data makes it possible to avoid carrying out such processing in a remote computer terminal.

Thus, the device according to the invention notably makes it possible to optimize the use of the energy resources by making a selective transmission of measurement data or of alert information possible, for example when the smart module diagnoses an anomaly.

Furthermore, such a device makes it possible to transmit anomaly information within a time delay that can be very short, even quasi-instantaneous, as soon as an anomaly is diagnosed by the device, rather than at regular time intervals.

Advantageously, the communication means comprise at least one transmitter compatible with reception systems available within the geographic perimeter of the distribution network, allowing a two-way communication between the smart module and the remote computer terminal.

In particular, the invention provides for the smart module to be able to be parameterized from the remote computer terminal.

Remote parameterization makes it possible to reduce the operational costs by avoiding the need for an operator wanting for example to re-parameterize or update software implemented in the smart module to go to the place of installation of the device.

According to another advantageous particular feature of the invention, the device further comprises a modular support element arranged to make it possible to position at least one sensor in such a way that its measurement end is received in the at least one insertion housing, this modular support element comprising fixing means for the at least one sensor capable of holding the at least one sensor in a measurement position in which the at least one sensor is able to measure the at least one physical, chemical or biological parameter of the fluid flowing through the flow pipe.

The modularity of the support element makes it possible to easily change a sensor, and to standardize the sensor fixing means.

According to other advantageous particular features, the at least one sensor is a sensor of flow rate type, and, possibly, the flow rate sensor is used as remote-reading meter.

The inclusion of the remote-reading function in such a device makes it possible to make savings on a conventional remote-reading meter installation. That also makes it possible to replace the metering function performed by a conventional meter with a measurement of a physical parameter of a fluid that is possibly more sensitive.

According to another advantageous particular feature, the measurement frequency of the at least one sensor is parameterizable, and this measurement frequency can be parameterized separately for each of the sensors when the device comprises several sensors.

In this way, the ratio between the energy expenditure required to perform a measurement and the relevant measurement frequency can be optimized.

According to yet another advantageous particular feature, the device further comprises an additional energy supply system capable of harvesting energy present in the environment in which the device is installed, a system for converting this harvested energy into electrical energy and a power supply system capable of powering the device with this electrical energy.

This particular feature makes it possible to increase the period of autonomy of the device.

The invention also relates to a method for installing such a device, characterized in that it comprises:
- a step of cutting of the pipe so as to produce an opening therein and form the first section and the second section,
- a step of positioning of the device by alignment of the first end of the flow pipe with an end of the first section and the second end of the flow pipe with an end of the second section,
- a step of fixing of the device in the aligned position described in the preceding step using the fixing means.

DESCRIPTION OF THE FIGURE AND OF EMBODIMENTS

Other advantages and particular features of the invention will become apparent on reading the detailed description of nonlimiting implementations and embodiments, and the attached FIG. 1 which represents an exemplary embodiment of the device according to the invention.

Since the embodiments described hereinbelow are non-limiting, it will notably be possible to consider variants of the invention comprising only a selection of features described, isolated from the other features described (even if this selection is isolated in a sentence comprising other features), if this selection of features is sufficient to confer a technical advantage or to differentiate the invention from the prior art. This selection comprises at least one feature, preferably functional without structural details, or with only some of the structural details if this part alone is sufficient to confer a technical advantage or to differentiate the invention from the prior art.

FIG. 1 represents the device according to a currently preferred embodiment of the invention.

In this example, the device comprises a body 21 enclosing, notably, sensors 11, 12, an electrical power supply system 61, 62, communication means 5 and a smart module 4.

Flow Pipe

The body 21 consists of a flow pipe 22 through which a fluid 9 flows (from left to right in FIG. 1). The flow pipe 22 is represented with partial cutaway revealing the interior of the flow pipe 22 in a region in which the sensors 11, 12 are located (see later).

The flow pipe 22 consists here of a tubular element of internal diameter S, for example made of polyvinyl chloride.

Assembly of the Device with a Pipe

The flow pipe 22 comprises two opposing ends 223, 224 extending out of the body 21. Threads 221, 222 are formed on the outer surface of the flow pipe 22 at its ends 223, 224. These screw-forming threads 221, 222 constitute fixing means making it possible to assemble the device with respective pipe sections, for example via coupling elements comprising a nut-forming internal threaded part.

These fixing means 221, 222 are used to assemble the flow pipe 22 in an inline position in a pipe. For example, a section of the pipe is cut over a length corresponding substantially to the length of the flow pipe 22, the flow pipe 22 is aligned with the pipe such that the flow pipe 22 is situated in place of the cut section, then the device is fixed via the fixing means 221, 222 and suitable couplings.

When the device is thus installed, the flow pipe 22 constitutes a part of the pipe such that, when a fluid 9 flows in the pipe from a point A situated upstream of the device to a point B situated downstream of the device, this fluid 9 flows through the flow pipe 22.

Sensors

The flow pipe 22 is represented secured to a modular support element 3 (FIG. 1). The modular support element 3 comprises orifices aligned with orifices of substantially identical dimension which are produced in the flow pipe 22. These orifices are insertion housings 31, 32, 33 arranged to receive sensors 11, 12. The insertion housing 33 is represented without sensor in FIG. 1.

The sensors 11, 12 are fixed to the modular support element 3 by any suitable fixing means which depend for example on the manufacture thereof. For example, the sensors 11, 12 have a partially threaded body making it possible to position them and screw them onto a nut formed in the insertion housings 31, 32, and lock nuts are used to hold the sensors 11, 12.

Referring to FIG. 1, the sensors 11, 12 are fixed in a position in which their measurement end, that is to say the end comprising a means sensitive to a parameter of the fluid 9, is situated inside the flow duct 22.

The sensors 11, 12 are preferably mounted tightly in the insertion housings 31, 32, for example by the use of O-ring seals, in order to avoid any of the fluid 9 penetrating into the space of the body 1 in which the smart module 4 is notably located.

The modular support element 3 is arranged to make it possible to mount one or more sensors in a modular fashion. Plugs can be provided to block the insertion housings not accommodating any sensor.

The sensors 11, 12 are for example sensors for measuring one or more physical properties of the water (e.g. volume, flow velocity, flow rate, pressure, noise level, etc.) or even sensors for measuring the quality of the water by quantifying chemical or biological parameters (e.g. temperature, chlorine, conductivity, dissolved oxygen, pH, redox potential, organic substances, micro-pollutants, metals, disinfectant by-products, etc.).

The sensors 11, 12 are connected to the smart module 4 by connection to the input/output manager 41.

Power Supply

The power supply system 61, 62 supplies electrical energy to the sensors 11, 12, to the communication means 5, to the smart module 4 and to electronic modules, for example conditioning, computation and storage electronic modules (not represented).

The power supply system 61, 62 ensures the supply of a current-stabilized voltage required by each of these modules, means and sensors.

The power supply system preferably comprises an electrical battery 62 linked to an energy management module 61 capable of transferring electrical energy to the smart module 4.

In an alternative embodiment, the energy management module 61 is linked to a storage battery 62 and to an additional energy supply system. In a nonlimiting manner, this system is an energy harvester, for example harvesting kinetic energy produced by the flow of the fluid 9 in the flow duct 22 using a turbine, or using energy harvested with a temperature differential between the duct and the cover of a roadway manhole.

Communication

The communication means 5 are arranged to exchange data between the smart module and a remote computer terminal or access point (private radio receiver or public network).

The remote computer terminal is for example situated in premises of the supplier of the fluid 9.

The communication means 5 are of a type capable of formatting data to be transmitted from the smart module to the computer terminal or access point and of decoding data received in accordance with a protocol for exchanging frames with the access point.

The communication means 5 can comprise a module for securing exchanges by techniques of encryption or authentication type.

Smart Module

The smart module 4, forming a processing unit, preferably comprises a processor and a memory that are capable of processing measurement data produced by the sensors 11, 12 and of scheduling the tasks to be performed by each of the components linked to the smart module 4.

Preferably, the smart module 4 comprises a real-time operating system and software codes capable of performing sophisticated processing operations, for example:
  conditioning signals measured by the sensors 11, 12,
  storing time-stamped samples for each measured parameter (configurable depth), detecting events on each temporal series of sensor measurements, specific processing such as:
triggering the sending of a temporal series when an event or an anomaly is detected,
applying, for example, statistical functions or spectral methods to a signal for a consolidation in models used by the operator of the device.

The smart module also includes a component capable of parameterizing or configuring the device.

For example, parameterizings can be performed by a computer terminal connected to the device locally via a physical connection, and parameterizings can be performed by a remote computer terminal communicating with the smart module using communication means 5 as described above.

Examples of remote actions are:
loading a specific processing code,
sampling frequency of the sensors 11, 12,
frequency of transmission of measurement data to a remote computer terminal,
type of processing or action when an event or an anomaly is detected,
updating of embedded software,
etc.

Obviously, the invention is not limited to the examples which have just been described and many improvements can be made to these examples without departing from the scope of the invention. Furthermore, the different features, forms, variants and embodiments of the invention can be associated with one another according to various combinations in as much as they are not mutually incompatible or exclusive.

The invention claimed is:

1. A device for measuring at least one physical, chemical or biological parameter of a fluid that is water or gas, flowing in a pipe belonging to a fluid distribution network, said device being configured to be installed as cutoff on said pipe at the point of delivery of the fluid, said pipe including a first section and a second section, said device comprising:
a plurality of sensors each provided with a measurement end configured to measure the at least one physical, chemical or biological parameter of the fluid flowing through the flow pipe;
a body comprising a flow pipe through which the fluid flows, the flow pipe comprising a plurality of flow pipe orifices;
a modular support element located within the body and comprising a plurality of spaced-apart insertion housings in the form of orifices, each insertion housing being aligned with one of the orifices of the flow pipe such that each of the sensors is configured to be inserted within the modular support element and extend through the respective insertion housing through the respective orifice of the flow pipe, the flow pipe being secured to the modular support element, said measurement end of each said sensor being received in a respective one of the insertion housings and extending through the respective insertion housing and the respective orifice of the flow pipe to protrude beyond the modular support element into the flow pipe;
a sensor fixing system that fixes each sensor in the respective one of the insertion housings, each sensor being held in a measurement position in which each sensor is operative to measure the at least one physical, chemical or biological parameter of the fluid flowing through the flow pipe;
a first fixing system configured to connect:
a first end of the flow pipe to an end of the first section, and
a second end of the flow pipe to an end of the second section,
to allow the fluid to flow through the flow pipe;
a smart module located within the body and configured to:
trigger at least one measurement by the plurality of sensors at determined time intervals, and
diagnose an anomaly of at least one physical, chemical or biological parameter of the fluid as a function of at least one measured value, the smart module comprising a communication system configured to carry out a computerized communication between the smart module and a remote computer terminal, the smart module being configured to transmit to the computer terminal information relating to the diagnosed anomaly; and
a component configured to parameterize or to configure the device by the remote computer terminal using the communication system,
wherein the sensors are mounted in a modular manner in the modular support element.

2. The device as claimed in claim 1, wherein said component is configured to parameterize:
one or more of a sampling frequency of each sensor, a frequency of transmission of measurement data to the remote computer terminal, and
a type of processing or an action when an event or an anomaly is detected.

3. The device as claimed in claim 2, further comprising an electric battery linked to an energy management module configured to transfer electrical energy to the smart module.

4. The device as claimed in claim 2, wherein the average internal section of the flow pipe is substantially identical to the average internal section of the pipe.

5. The device as claimed in claim 1, further comprising an electric battery linked to an energy management module configured to transfer electrical energy to the smart module.

6. The device as claimed in claim 5, wherein the energy management module is linked to a storage battery and to an additional energy supply system.

7. The device as claimed in claim 6, wherein the additional energy supply system is configured to harvest kinetic energy produced by the flow of the fluid in the flow pipe using a turbine.

8. The device as claimed in claim 6, wherein the additional energy supply system is configured to harvest energy via a temperature differential between the pipe and a roadway manhole cover.

9. The device as claimed in claim 5, wherein the average internal section of the flow pipe is substantially identical to the average internal section of the pipe.

10. The device as claimed in claim 1, wherein the average internal section of the flow pipe is substantially identical to the average internal section of the pipe.

11. The device as claimed in claim 1, wherein the instant of the transmission of the information relating to the diagnosed anomaly is determined by the instant at which said anomaly is diagnosed.

12. The device as claimed in claim 1, wherein the communication system comprises at least one transmitter compatible with a receiver available within the geographic perimeter of the distribution network, allowing a two-way communication between the smart module and the remote computer terminal.

13. The device as claimed in claim 1, further comprising an additional energy supply system configured to harvest energy present in the environment in which the device is installed, a conversion system configured to convert the harvested energy into electrical energy and a power supply system configured to power the device with the electrical energy.

14. The device of claim 1, wherein the plurality of sensors includes a fluid flow rate sensor.

15. The device of claim 1, wherein the plurality of sensors includes at least a first sensor that measures a physical parameter of the water selected from the group consisting of volume, flow velocity, flow rate, pressure, and noise level.

16. A device for measuring at least one physical, chemical or biological parameter of a fluid that is water or gas, flowing in a pipe belonging to a fluid distribution network, said device being configured to be installed as cutoff on said pipe at the point of delivery of the fluid, said pipe including a first section and a second section, said device comprising:
- a plurality of sensors each provided with a measurement end configured to measure the at least one physical, chemical or biological parameter of the fluid flowing through the flow pipe;
- a body comprising a flow pipe through which the fluid flows, the flow pipe comprising a plurality of flow pipe orifices;
- a modular support element located within the body and comprising a plurality of spaced-apart insertion housings in the form of orifices, each insertion housing being aligned with one of the orifices of the flow pipe such that each of the sensors is configured to extend through the respective insertion housing through the respective orifice of the flow pipe, the flow pipe being secured to the modular support element, said measurement end of each said sensor being received in a respective one of the insertion housings and extending through the respective insertion housing and the respective orifice of the flow pipe to emerge in the flow pipe;
- a sensor fixing system that fixes each sensor in the respective one of the insertion housings, each sensor being held in a measurement position in which each sensor is operative to measure the at least one physical, chemical or biological parameter of the fluid flowing through the flow pipe;
- a first fixing system configured to connect:
  - a first end of the flow pipe to an end of the first section, and
  - a second end of the flow pipe to an end of the second section,
  - to allow the fluid to flow through the flow pipe;
- a smart module located within the body and configured to:
  - trigger at least one measurement by the plurality of sensors at determined time intervals, and
  - diagnose an anomaly of at least one physical, chemical or biological parameter of the fluid as a function of at least one measured value, the smart module comprising a communication system configured to carry out a computerized communication between the smart module and a remote computer terminal, the smart module being configured to transmit to the computer terminal information relating to the diagnosed anomaly; and
- a component configured to parameterize or to configure the device by the remote computer terminal using the communication system,
- wherein the measurement frequency of each sensor is parameterizable, and
- wherein the measurement frequency is parameterized separately for each of the sensors.

17. A device for measuring at least one physical, chemical or biological parameter of a fluid, including water or gas, flowing in a pipe belonging to a fluid distribution network and a first section and a second section, said device being intended to be installed as cutoff on said pipe at the point of delivery of the fluid, said device comprising:
- a plurality of sensors provided with a measurement end, the measurement end of each sensor being configured to measure the at least one physical, chemical or biological parameter of the fluid flowing through the flow pipe;
- a flow pipe comprising a plurality of first orifices, said measurement end of each sensor extending, via one of the first orifices of the flow pipe, into the flow pipe;
- first and second connections configured to respectively connect a first end of the flow pipe to an end of the first section and to connect a second end of the flow pipe to an end of the second section, to allow the fluid to flow through the flow pipe;
- a body housing a modular support element and a smart module, the smart module being configured to
  - trigger at least one measurement by each sensor at determined time intervals, and
  - diagnose an anomaly of at least one physical, chemical or biological parameter of the fluid as a function of at least one measured value,
- the smart module comprising:
  - a communication system configured to carry out a computerized communication between the smart module and a remote computer terminal, the smart module being configured to transmit to the computer terminal information relating to the diagnosed anomaly,
  - a component configured to parameterize or configure the device by the remote computer terminal using the communication module,
- the modular support element comprising
  - a plurality of spaced-apart second orifices, each second orifice aligned with a respective one of the first orifices of flow pipe such that each of the sensors is configured to be inserted within the modular support element and extend through the respective second orifice and through the respective first orifice of the flow pipe, each second orifice forming an insertion housing in which a first one of the sensors is received and extends through the respective insertion housing and the respective orifice of the flow pipe to protrude beyond the modular support element into the flow pipe, and
  - fixing elements that fix each sensor in a corresponding one of the second orifices of the modular support element with each sensor being positioned such that the measurement end of each sensor is received in one first orifice of the flow pipe with the measurement end of each sensor being positioned in a measurement position in which each sensor is configured to measure the at least one physical, chemical or biological parameter of the fluid flowing through the flow pipe,
  - the flow pipe being secured to the modular support element,
  - each fixing element being configured to remove each sensor from the corresponding one second orifice in which each sensor is received and to replace each sensor with a new sensor fixed in the corresponding one second orifice forming the insertion housing with the new sensor being positioned with the measurement end of the new sensor being positioned in the measurement position to measure the at least one physical, chemical or biological parameter of the fluid flowing through the flow pipe, wherein the new sensor measures a different one of the at least one physical, chemical or biological parameter of the fluid than the sensor having been removed, and wherein the sensors are mounted in a modular manner in the modular support element.

18. The device of claim 17, wherein, the sensor having been removed measures a first physical parameter of the water selected from the group consisting of volume, flow velocity, flow rate, pressure, and noise level, or measures a first quantifying chemical or biological parameter selected from the group consisting of temperature, chlorine, conductivity, dissolved oxygen, pH, redox potential, organic substances, micro-pollutants, metals, and disinfectant by-products, and the new sensor measures a second physical parameter of the water selected from the group consisting of volume, flow velocity, flow rate, pressure, and noise level, or measures a second quantifying chemical or biological parameter selected from the group consisting of temperature, chlorine, conductivity, dissolved oxygen, pH, redox potential, organic substances, micro-pollutants, metals, and disinfectant by-products, the second physical parameter and the second quantifying chemical or biological parameter being different from the first physical parameter and the first quantifying chemical or biological parameter.

19. A device for measuring at least one physical, chemical or biological parameter of a fluid that is water or gas, flowing in a pipe belonging to a fluid distribution network, said device being configured to be installed as cutoff on said pipe at the point of delivery of the fluid, said pipe including a first section and a second section, said device comprising:

a plurality of sensors each provided with a measurement end configured to measure the at least one physical, chemical or biological parameter of the fluid flowing through the flow pipe;

a body comprising a flow pipe through which the fluid flows, the flow pipe comprising a plurality of flow pipe orifices;

a modular support element located within the body and comprising a plurality of spaced-apart insertion housings in the form of orifices, each insertion housing being aligned with one of the orifices of the flow pipe, the flow pipe being secured to the modular support element, said measurement end of each said sensor being received in a respective one of the insertion housings and emerging in the flow pipe;

a sensor fixing system that fixes each sensor in the respective one of the insertion housings, each sensor being held in a measurement position in which each sensor is operative to measure the at least one physical, chemical or biological parameter of the fluid flowing through the flow duct;

a first fixing system configured to connect:
 a first end of the flow pipe to an end of the first section, and
 a second end of the flow pipe to an end of the second section,
 to allow the fluid to flow through the flow pipe;

a smart module located within the body and configured to:
 trigger at least one measurement by the plurality of sensors at determined time intervals, and
 diagnose an anomaly of at least one physical, chemical or biological parameter of the fluid as a function of at least one measured value, the smart module comprising a communication system configured to carry out a computerized communication between the smart module and a remote computer terminal, the smart module being configured to transmit to the computer terminal information relating to the diagnosed anomaly; and a component configured to parameterize or to configure the device by the remote computer terminal using the communication system,
 wherein the plurality of sensors includes at least a first sensor that measures a quantifying chemical or biological parameter selected from the group consisting of temperature, chlorine, conductivity, dissolved oxygen, pH, redox potential, organic substances, micro-pollutants, metals, and disinfectant by-products.

20. A device for measuring at least one physical, chemical or biological parameter of a fluid that is water or gas, flowing in a pipe belonging to a fluid distribution network, said device being configured to be installed as cutoff on said pipe at the point of delivery of the fluid, said pipe including a first section and a second section, said device comprising:

a plurality of sensors each provided with a measurement end configured to measure the at least one physical, chemical or biological parameter of the fluid flowing through the flow pipe;

a body comprising a flow pipe through which the fluid flows, the flow pipe comprising a plurality of flow pipe orifices;

a modular support element located within the body and comprising a plurality of spaced-apart insertion housings in the form of orifices, each insertion housing being aligned with one of the orifices of the flow pipe, the flow pipe being secured to the modular support element, said measurement end of each said sensor being received in a respective one of the insertion housings and emerging in the flow pipe;

a sensor fixing system that fixes each sensor in the respective one of the insertion housings, each sensor being held in a measurement position in which each sensor is operative to measure the at least one physical, chemical or biological parameter of the fluid flowing through the flow pipe;

a first fixing system configured to connect:
 a first end of the flow pipe to an end of the first section, and
 a second end of the flow pipe to an end of the second section,
 to allow the fluid to flow through the flow pipe;

a smart module located within the body and configured to:
 trigger at least one measurement by the plurality of sensors at determined time intervals, and
 diagnose an anomaly of at least one physical, chemical or biological parameter of the fluid as a function of at least one measured value, the smart module comprising a communication system configured to carry out a computerized communication between the smart module and a remote computer terminal, the smart module being configured to transmit to the computer terminal information relating to the diagnosed anomaly; and a component configured to parameterize or to configure the device by the remote computer terminal using the communication system, wherein the plurality of sensors include a first sensor that measures a physical parameter of the water selected from the group consisting of volume, flow velocity, flow rate, pressure, and noise level, and a second sensor that measures a quantifying chemical or biological parameter selected from the group consisting of temperature, chlorine, conductivity, dissolved oxygen, pH, redox potential, organic substances, micro-pollutants, metals, and disinfectant by-products.

* * * * *